United States Patent
Salah et al.

(10) Patent No.: US 11,419,699 B2
(45) Date of Patent: Aug. 23, 2022

(54) METHOD OF DETERMINING AN ORTHODONTIC TREATMENT

(71) Applicant: DENTAL MONITORING, Paris (FR)

(72) Inventors: Philippe Salah, Bagnolet (FR);
Thomas Pellissard, Clichy (FR);
Guillaume Ghyselinck, Cantin (FR);
Laurent Debraux, Paris (FR)

(73) Assignee: DENTAL MONITORING, Paris (FR)

( * ) Notice: Subject to any disclaimer, the term of this patent is extended or adjusted under 35 U.S.C. 154(b) by 343 days.

(21) Appl. No.: 15/990,950

(22) Filed: May 29, 2018

(65) Prior Publication Data

US 2018/0344430 A1 Dec. 6, 2018

(30) Foreign Application Priority Data

May 30, 2017 (FR) .................................... 1754755

(51) Int. Cl.
*A61C 7/00* (2006.01)
*G16H 50/50* (2018.01)
(Continued)

(52) U.S. Cl.
CPC .............. *A61C 7/002* (2013.01); *A61C 7/08* (2013.01); *A61C 7/12* (2013.01); *A61C 9/004* (2013.01);
(Continued)

(58) Field of Classification Search
CPC ................. A61C 7/08; A61C 7/002
See application file for complete search history.

(56) References Cited

U.S. PATENT DOCUMENTS

| 7,074,038 B1 * | 7/2006 | Miller | A61C 7/08 |
| | | | 433/24 |
| 8,562,338 B2 * | 10/2013 | Kitching | A61C 7/002 |
| | | | 433/24 |

(Continued)

FOREIGN PATENT DOCUMENTS

FR 3027505 A1 4/2016
WO 2016066642 A1 5/2016

OTHER PUBLICATIONS

Corresponding French Application, French Search Report, Application No. 1754755, dated Feb. 7, 2018, 2 pages.

*Primary Examiner* — Ralph A Lewis
(74) *Attorney, Agent, or Firm* — Ronald M. Kachmarik; Cooper Legal Group LLC (57) ABSTRACT

A method of determining an optimal switchover moment for a hybrid orthodontic treatment of teeth. Creation of a digital three-dimensional model of at least part of a dental arch. Deformation of the initial reference model until the tooth models are in a target position. Acquisition of at least one two-dimensional image of the teeth. Deformation of the initial reference model until the at least one updated image corresponds to the initial reference model. Determination, from the updated reference model and from said target reference model, of a plurality of remaining-treatments for moving the teeth from their position represented in the updated reference model into their position represented in the target reference model. Determination of a profile including at least one value for an evaluation parameter. Evaluation of each profile by an evaluation rule. Determination the profile of which is optimal for replacing an orthodontic appliance with an aligner.

15 Claims, 1 Drawing Sheet

(51) Int. Cl.
*G16H 50/20* (2018.01)
*G16H 20/40* (2018.01)
*G16H 20/30* (2018.01)
*A61C 7/08* (2006.01)
*A61C 7/12* (2006.01)
*A61C 9/00* (2006.01)
*G06T 17/00* (2006.01)
*G06T 19/20* (2011.01)

(52) U.S. Cl.
CPC .............. *G06T 17/00* (2013.01); *G06T 19/20* (2013.01); *G16H 20/30* (2018.01); *G16H 20/40* (2018.01); *G16H 50/20* (2018.01); *G16H 50/50* (2018.01); *G06T 2219/2004* (2013.01)

(56) References Cited

U.S. PATENT DOCUMENTS

| | | | | |
|---|---|---|---|---|
| 8,636,509 B2* | 1/2014 | Miller | ............... | A61C 7/12 |
| | | | | 433/24 |
| 8,961,173 B2* | 2/2015 | Miller | ............... | A61C 7/00 |
| | | | | 433/24 |
| 9,022,781 B2* | 5/2015 | Kuo | ............... | A61C 7/002 |
| | | | | 433/24 |
| 9,333,052 B2* | 5/2016 | Miller | ............... | A61C 7/20 |
| 9,642,678 B2* | 5/2017 | Kuo | ............... | A61C 7/002 |
| 10,052,174 B2* | 8/2018 | Kitching | ............... | A61C 7/002 |
| 10,507,079 B2* | 12/2019 | Miller | ............... | A61C 7/146 |
| 2005/0026102 A1 | 2/2005 | Miller | | |
| 2016/0228212 A1 | 8/2016 | Salah et al. | | |
| 2016/0310235 A1 | 10/2016 | Derakhshan et al. | | |

\* cited by examiner

METHOD OF DETERMINING AN ORTHODONTIC TREATMENT

TECHNICAL FIELD

The present invention relates to a method of determining a switchover moment beyond which a patient wearing an arch wire and brackets orthodontic appliance will switch over to wearing one or more orthodontic aligners.

The invention also relates to a computer program for implementing this method.

PRIOR ART

Among orthodontic appliances, a distinction is made between, on the one hand, arch wire and brackets orthodontic appliances and, on the other hand, orthodontic aligners.

An orthodontic appliance with arch wire and brackets comprises fixings, referred to as "brackets", fixed to the teeth and connected to one another by means of an arch wire, conventionally made from a shape-memory material. It acts quickly to move the teeth of the patient being treated. However, this action slows progressively over time and the patient needs to visit the orthodontist regularly in order to modify the adjustment of the arch wire, or change same. Furthermore, an orthodontic appliance of the arch wire and brackets type is often visually unattractive.

A tray-like device, more properly known as an "aligner", conventionally comes in the form of a removable monobloc appliance, conventionally made of a transparent polymer. It comprises a tray shaped in such a way that several teeth of a dental arch, generally all the teeth of a dental arch, can be housed therein. The shape of the tray is tailored to hold the aligner in position on the teeth while at the same time applying an action towards correcting the positioning of certain teeth. An orthodontic aligner has an initial action that is far slower than that of an arch wire and brackets orthodontic appliance. However, the aligner may advantageously be replaced by the patient himself. Furthermore, aligners are more discreet than arch wire and brackets appliances.

A "hybrid" orthodontic treatment makes it possible to enjoy the advantages of each of these two types of orthodontic appliance. Usually, it comprises a first treatment phase during which the patient wears an orthodontic appliance or "arch wire phase", followed, from a switchover moment onwards, by a second phase of treatment using orthodontic aligners, or "aligners phase". The treatment then continues using aligners.

There is constantly a need for a method that makes it possible to optimize a hybrid treatment, particularly in order to reduce the duration thereof.

One object of the invention is to provide a response to this need.

SUMMARY OF THE INVENTION

The invention provides a method of determining an optimal switchover moment for a hybrid orthodontic treatment of teeth of a patient, said method comprising the following operations:

1) for preference at the start of the treatment or before the start of the treatment, creation of a digital three-dimensional model of at least part of a dental arch bearing said teeth, or "initial reference model" and, for each of said teeth, definition of a digital three-dimensional reference model of said tooth in the initial reference model, or "tooth model";
2) after operation 1), preferably at the start of the treatment or before the start of the treatment, deformation of the initial reference model, by moving the tooth models, until said tooth models are in a target position, so as to obtain a "target reference model",
3) after operation 2), at some moment in a phase of the treatment during which the patient wears an arch wire and brackets orthodontic appliance, referred to as "current moment", acquisition of at least one two-dimensional image of said teeth, referred to as "updated image", under the actual acquisition conditions;
4) deformation of the initial reference model, by moving the tooth models, until said at least one updated image corresponds to a view of the initial reference model thus deformed, referred to as "updated reference model", the search for the updated reference model preferably being performed by means of a meta-heuristic, preferably evolutionary method, preferably by simulated annealing;
5) determination, from said updated reference model and from said target reference model, of a plurality of remaining-treatment scenarios for moving said teeth from their position represented in the updated reference model into their position represented in the target reference model, each scenario comprising, from a switchover moment onwards, at least one phase of treatment using an orthodontic aligner;
6) determination, for each scenario, of a profile comprising at least one value for an evaluation parameter selected from the group formed of:
   the duration of the remaining treatment of said scenario;
   the duration of the entire treatment;
   a clinical-complexity factor, or "severity score";
   a pain factor for the remaining treatment of said scenario,
   a pain factor for the entire treatment;
   the duration of the phase or phases of treatment using an arch wire and brackets orthodontic arch wire during the remaining treatment;
   a comfort factor for the remaining treatment of said scenario,
   a comfort factor for the entire treatment;
   a cost of the remaining treatment of said scenario,
   a cost of the entire treatment,
   a function of the preceding evaluation parameters;
7) evaluation of each profile by means of an evaluation rule; and
8) determination, from the scenario the profile of which is optimal, or "optimal scenario" of an optimal switchover moment for replacing the arch wire and brackets orthodontic appliance with an aligner.

As will be seen in greater detail in what follows of the description, a method according to the invention allows the treatment to be adapted to suit specific conditions, and in particular, conditions imposed by the patient. For example, if the patient imposes a maximum treatment duration of six months and an aligner phase that is as long as possible, the method according to the invention makes it possible to test various scenarios in order to search for the profile that best meets this need.

Operations 5) to 8) may or may not be successive. When they are successive, they are referred to as "steps" 5') to 8') respectively.

In a preferred embodiment, they are imbricated and constitute the following successive steps 5") to 8"):
- 5") determination, from said updated reference model and from said target reference model, of a remaining-treatment scenario for moving said teeth from their position represented in the updated reference model into their position represented in the target reference model, a remaining-treatment scenario comprising, from a switchover moment onwards, at least one phase of treatment using an orthodontic aligner;
- 6") determination, for said scenario, of a profile comprising at least one value for an evaluation parameter selected from the group formed of:
  - the duration of the remaining treatment of said scenario;
  - the duration of the entire treatment;
  - a clinical-complexity factor, or "severity score";
  - a pain factor for the remaining treatment of said scenario;
  - a clinical-complexity factor;
  - a pain factor for the entire treatment;
  - the duration of the phase or phases of treatment using an arch wire and brackets orthodontic arch wire during the remaining treatment;
  - a comfort factor for the remaining treatment of said scenario,
  - a comfort factor for the entire treatment;
  - a cost of the remaining treatment of said scenario,
  - a cost of the entire treatment,
  - a function of the preceding evaluation parameters;
- 7") evaluation of the profile by means of an evaluation rule and, if the profile is not optimal with reference to the evaluation rule, determination of a new remaining-treatment scenario and resumption from step 6");
- 8") determination, from the scenario the profile of which is optimal, or "optimal scenario" of an optimal switchover moment for replacing the arch wire and brackets orthodontic appliance with an aligner.

For preference, a method according to the invention also has one or more of the following optional features:
- over 5, 10, 50 or 100 scenarios are determined in operation 5);
- in operation 3), the updated image is taken by means of an image acquisition apparatus selected from the group consisting of a mobile telephone, a connected camera, a smartwatch, a tablet and/or a desktop or laptop personal computer;
- operation 4) comprises the following steps:
  - c) analysis of the updated image and creation of an updated map relating to discriminating information;
  - d) optionally, determination, for the updated image, of rough virtual acquisition conditions approximating the actual acquisition conditions of said updated image;
  - e) search, in the case of the updated image, for an updated reference model corresponding to the positioning of the teeth at the time of the acquisition of the updated image, the search preferably being carried out by means of a meta-heuristic, preferably evolutionary method, preferably by simulated annealing.
- step e) comprises the following steps:
  - e1) definition of a reference model to be tested as being the initial reference model, then
  - e2) following the subsequent steps, testing virtual acquisition conditions with the reference model to be tested in order to achieve a fine approximation of said actual acquisition conditions;
  - e21) determining virtual acquisition conditions to be tested;
  - e22) creation of a two-dimensional reference image of the reference model to be tested under said virtual acquisition conditions to be tested;
  - e23) processing of the reference image to create at least a reference map at least partially representing said discriminating information;
  - e24) comparison of the updated and reference maps so as to determine a value for a first evaluation function, said value for the first evaluation function being dependent on the differences between said updated and reference maps and corresponding to a decision as to whether to continue or stop the search for virtual acquisition conditions approximating said actual acquisition conditions with greater precision than said virtual acquisition conditions to be tested as determined the last time step e21) was run;
  - e25) if said value for the first evaluation function corresponds to a decision to continue said search, modification of the virtual acquisition conditions to be tested, then resumption from step e22);
  - e3) determination of a value for a second evaluation function, said value for the second evaluation function being dependent on the differences between the updated and reference maps under the virtual acquisition conditions best approximating said actual acquisition conditions and resulting from the last running of step e2), said value for the second evaluation function corresponding to a decision to continue or stop the search for a reference model approximating the positioning of the teeth at the time of the acquisition of the updated image with greater precision than said reference model to be tested that was used the last time step e2) was run, and if said value for the second evaluation function corresponds to a decision to continue said search, modification of the reference model to be tested by moving one or more tooth models, followed by resumption from step e2);
- the method comprises a step 9) in which the optimal switchover moment, preferably the optimal scenario and/or the optimal profile, are presented to a doctor, particularly an orthodontist, and/or to the patient;
- in step 1), a digital three-dimensional reference model is defined for a gum from which said tooth models emerge, or "gum model", and, in step 4), said tooth models are moved and said gum model is modified to deform the initial reference model;
- in order to deform the initial reference model a deformation of the gum model is calculated from said movements of said tooth models;

Preferably, operations 4) and/or 5) and/or 6) and/or 7) and/or 8), preferably at least steps 4) and 5) and preferably 6), and preferably 7), and preferably 8) are achieved with a computer;

preferably, an orthodontist commands the computer at step 2).

The invention also relates to a method of adapting an orthodontic aligner, in which method a method for determining an optimal switchover moment according to the invention is implemented and then, according to the result of said evaluation, an aligner suited to at least part of the orthodontic treatment of the teeth onwards from said optimal switchover moment is manufactured.

The invention also relates to:
- a computer program and, in particular, a specialist application for a mobile telephone, comprising program code instructions for executing one or more, preferably all, of operations 3) to 8) when said program is run by a computer,
- a computer medium on which such a program is recorded, for example a memory or a CD-ROM; and
- a computation tool, particularly a personal device, in particular a mobile telephone or a tablet, on which such a program is loaded.

For preference, the computation tool comprises a scenario simulator able to create scenarios, to determine profiles of said scenarios, and to evaluate said scenarios with reference to an evaluation rule. For preference also, it comprises a "man-machine" interface and means for determining the evaluation rule from data input using said interface.

The invention also relates to a system comprising
- a three-dimensional scanner capable of creating an initial reference model, and
- a computation tool, particularly a personal device, preferably a mobile telephone, able to acquire an updated image and loaded with a program according to the invention.

Definitions

"Remaining treatment" is understood to mean that part of the treatment onwards from the current moment.

A "patient" is understood to mean any person for whom a method according to invention is implemented, whether this person is sick or not.

The "acquisition conditions" specify the position and the orientation in space of an image acquisition apparatus relative to the patient's teeth (actual acquisition conditions) or to a three-dimensional model of teeth of the patient (virtual acquisition conditions), and preferably the calibration of this image acquisition apparatus. Acquisition conditions are said to be "virtual", or "simulated" when they correspond to a simulation in which the acquisition apparatus would be under said acquisition conditions (virtual positioning and preferably virtual calibration of the acquisition apparatus).

The "calibration" of an acquisition apparatus consists of the set of values of the calibration parameters. A "calibration parameter" is a parameter intrinsic to the acquisition apparatus (unlike its position and its orientation), the value of which influences the image acquired.

Preferably, the calibration parameters are chosen from the group formed by the aperture, the exposure time, the focal length and the sensitivity.

A 3-D scanner is an apparatus that makes it possible to obtain a three-dimensional representation of an object.

What is meant by an "image" is a two-dimensional image such as a photograph. An image is made up of pixels.

An updated image "corresponds to" a view of the updated reference model when this view is substantially identical to said updated image.

The terms "comprise", "include" or "have" should be interpreted broadly and without limitation, unless specified otherwise.

BRIEF DESCRIPTION OF THE FIGURES

Additional features and advantages of the invention will become further apparent upon reading the following detailed description and from studying the attached drawing, in which.

DETAILED DESCRIPTION

Operation 1) is preferably performed at the start of the treatment or before the start of the treatment and consists in creating a digital three-dimensional model of a dental arch bearing the teeth treated, or "initial reference model".

The initial reference model is, for example, of the .stl or .Obj, .DXF 3D, IGES, STEP, VDA, or scattergram type. Advantageously, such a model, referred to as a "3-D" model, may be viewed from any angle.

The initial reference model may be prepared from measurements taken from the teeth of the patient or from a physical model of his teeth, for example a plaster cast.

The initial reference model is preferably created by means of a professional device, for example by means of a 3-D scanner, preferably operated by a healthcare professional, for example by an orthodontist, or an orthodontistry laboratory. In an orthodontist practice, the patient or the physical model of his teeth may advantageously be arranged in a precise position and the professional device may be perfected. This results in a highly accurate initial reference model. The initial reference model preferably provides information regarding the positioning of the teeth with an error of less than $5/10$ mm, preferably less than $3/10$ mm, preferably less than $1/10$ mm.

In the initial reference model, a part which corresponds to a tooth, or "tooth model" is delimited by a gum edge which may be broken down into an interior gum edge (on the side of the inside of the mouth in relation to the tooth), an exterior gum edge (facing toward the outside of the mouth in relation to the tooth) and two lateral gum edges. The tooth models may be defined as described, for example, in international application PCT/EP2015/074896.

For preference, the initial reference model also models the gum surrounding the teeth. The part of the initial reference model that represents the gum is referred to as the "gum model".

Operation 2) comprises modifying the initial reference model, by moving the tooth models, until a desired positioning of the teeth referred to as "target positioning" is obtained. The target positioning may be the one desired at the end of the treatment ("final set-up") or at a predetermined intermediate stage in the treatment ("intermediate set-up"). For preference, operation 2) also comprises a deforming of the gum model. In one preferred embodiment, the deformation of the gum model is, at least in part, the result of a simulation obtained from the moving of the tooth models. Advantageously, the search for the updated reference model is thereby speeded up.

For preference, operation 2), subsequent to operation 1), is performed immediately after operation 1).

Operations 3) and 4), subsequent to operation 2) have the objective of updating the initial reference model so that the tooth models are in positionings identical to those of the actual teeth at the current moment.

In operation 3), an updated image of the part of the dental arch bearing the teeth that are to be treated is taken, by means of an image acquisition apparatus, under actual acquisition conditions.

The image acquisition apparatus is preferably a mobile telephone, a "connected" camera, a smartwatch, a tablet or a desktop or laptop personal computer, including an image acquisition system, such as a webcam or a camera.

The acquisition is preferably performed by the patient or someone close to the patient, but may be performed by any other individual, notably a dentist or an orthodontist, preferably without imposing a requirement for the image acquisition apparatus to be positioned accurately with respect to the teeth.

For preference, the updated image is a photograph or an extract from a film. It is preferably in color, preferably true color.

For preference, in operation 3), the procedure is in accordance with step b) described in PCT/EP2015/074896.

Operation 4), subsequent to operation 3), preferably consists in an iterative process in which, upon each iteration, one or more tooth models are moved, then optimum conditions for observing the initial reference model thus modified (referred to as the "reference model to be tested") are determined, the optimum observation conditions being defined as the conditions allowing the reference model to be tested to be observed in such a way that the view of said model is as close as possible to the updated image.

For preference, on each iteration, the gum model is also deformed so that the initial reference model modified by the movement of the tooth models and the deformation of the gum model is as compatible as possible with the updated image.

In one embodiment, a first deformation of the gum model is calculated according to the movement of the tooth models. The first deformation may be sufficient. Otherwise, it is supplemented by a second deformation, preferably determined by means of a meta-heuristic, preferably evolutionary, method, preferably by simulated annealing.

Steps c) to e) described in PCT/EP2015/074896 are preferably implemented:
c) analysis of the updated image and creation of an updated map relating to discriminating information;
d) optionally, determination, for the updated image, of rough virtual acquisition conditions approximating the actual acquisition conditions of said updated image;
e) search, in the case of the updated image, for an updated reference model corresponding to the positioning of the teeth at the time of the acquisition of the updated image, the search preferably being carried out by means of a meta-heuristic, preferably evolutionary method, preferably by simulated annealing.

All the features of steps c) to e) described in PCT/EP2015/074896 are applicable.

According to step c), the updated image is analyzed so as to create an updated map relating to at least one item of discriminating information.

"Discriminating information" is characteristic information that can be extracted from an image ("image feature"), conventionally through the computer processing of this image.

Discriminating information may exhibit a variable number of values. For example, outline information may be equal to 1 or 0 according to whether or not a pixel belongs to an outline. Brightness information may adopt a great many values. Image processing makes it possible to extract and quantify the discriminating information.

The updated map represents discriminating information in the frame of reference of the updated image. The discriminating information is preferably chosen from the group consisting of outline information, color information, density information, distance information, brightness information, saturation information, information regarding reflections and combinations of this information.

In optional step d), the actual acquisition conditions for the updated image acquired in operation 3), namely the position and the orientation in space of the acquisition apparatus with respect to the teeth and the calibration thereof are evaluated, roughly. Step d) advantageously makes it possible to limit the number of tests on virtual acquisition conditions during step e) and therefore allows step e) to be speeded up considerably.

Use is preferably made of one or more heuristic rules. For example, for preference, conditions that correspond to a position of the image acquisition apparatus behind the teeth or at a distance greater than 1 m away from the teeth, are excluded from the virtual acquisition conditions that can be tested for in step e). In a preferred embodiment, use is made of markers marked on the updated image in order to determine a substantially conical region of the space that delimits the virtual acquisition conditions that can be tested for in step e), or "test cone".

The objective of step e) is to modify the initial reference model until there is obtained an updated reference model that corresponds to the updated image, namely such that the tooth models can be observed as depicted in the updated image. Ideally, the updated reference model is therefore a digital three-dimensional reference model from which the updated image could have been taken had this model been real.

A succession of reference models "to be tested" is therefore tested, the choice of a reference model to be tested being dependent preferably on the level of correspondence between the previously tested reference models "to be tested" and the updated image. This choice is preferably made by following a known optimization method, particularly chosen from meta-heuristic optimization methods, preferably evolutionary methods, particularly from simulated annealing methods. The optimization methods described in PCT/EP2015/074896 can notably be used.

For preference, step e) comprises the following steps:
e1) definition of a reference model to be tested as being the initial reference model, then
e2) following the subsequent steps, testing virtual acquisition conditions with the reference model to be tested in order to achieve a fine approximation of said actual acquisition conditions;
  e21) determining virtual acquisition conditions to be tested;
  e22) creation of a two-dimensional reference image of the reference model to be tested under said virtual acquisition conditions to be tested;
  e23) processing of the reference image to create at least a reference map at least partially representing said discriminating information;
  e24) comparison of the updated and reference maps so as to determine a value for a first evaluation function, said value for the first evaluation function being dependent on the differences between said updated and reference maps and corresponding to a decision as to whether to continue or stop the search for virtual acquisition conditions approximating said actual acquisition conditions with greater precision than said virtual acquisition conditions to be tested as determined the last time step e21) was run;
  e25) if said value for the first evaluation function corresponds to a decision to continue said search, modification of the virtual acquisition conditions to be tested, then resumption from step e22);

e3) determination of a value for a second evaluation function, said value for the second evaluation function being dependent on the differences between the updated and reference maps under the virtual acquisition conditions best approximating said actual acquisition conditions and resulting from the last running of step e2), said value for the second evaluation function corresponding to a decision to continue or stop the search for a reference model approximating the positioning of the teeth at the time of the acquisition of the updated image with greater precision than said reference model to be tested that was used the last time step e2) was run, and if said value for the second evaluation function corresponds to a decision to continue said search, modification of the reference model to be tested by moving one or more tooth models, followed by resumption from step e2).

Steps e1) to e3) are described in detail in PCT/EP2015/074896, or WO2016066651.

According to steps c) to e), the updated reference model is a three-dimensional model resulting from successive modifications to the very precise initial reference model. Advantageously, it is thus itself very precise, even though it has been obtained from simple photographs taken without any special precautions.

These steps therefore make it possible, starting from one or more simple images of teeth, taken without precisely pre-positioning the image acquisition apparatus with respect to the teeth, for example from a photograph taken by the patient, to assess with precision the position of the teeth at the current moment. This assessment may further be done remotely, from simple photographs taken on a mobile telephone, without the patient having to travel to the orthodontist's in person.

Operation 4) leads to an updated reference model representing the teeth very precisely, in the position they occupy at the current moment.

According to a first embodiment, the method continues with the succession of steps 5') to 8'):

In step 5'), a set of remaining-treatment scenarios, namely scenarios suitable for achieving a tooth positioning site substantially identical to that of the corresponding tooth models in the target reference model is determined.

Figure 1:
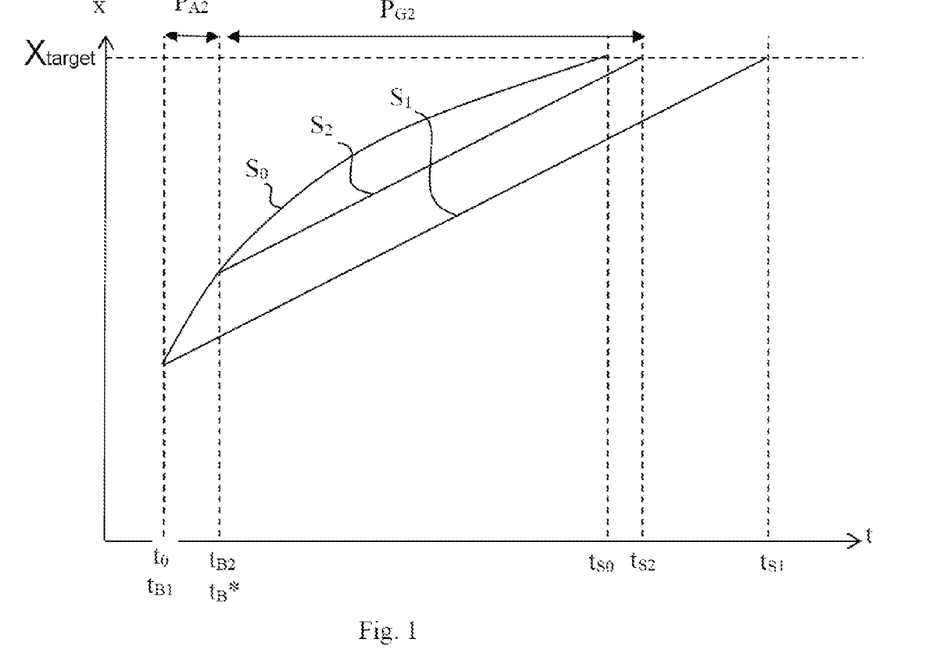
FIG. 1 depicts various evolutions with respect to time for a positioning parameter relating to the positioning of a tooth, according to the nature of the remaining treatment considered.
Figure 2:
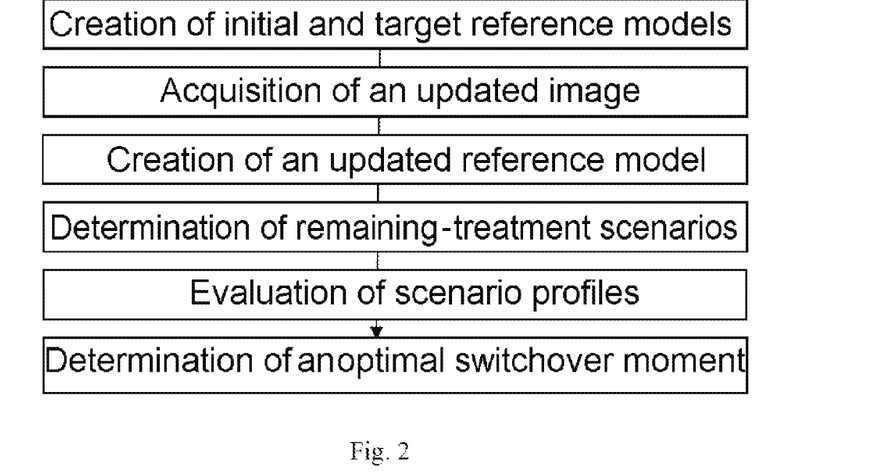
FIG. 2 is a flow diagram illustrating the implementation of a prediction method according to the invention.

FIG. 1 depicts for example three evolutions with respect to time of the coordinate x of a point on a tooth in space, as a function of the remaining treatment, namely of the treatment adopted onwards of the current moment $t_0$. The target positioning of this point is achieved when x is equal to $x_{target}$.

Curve $S_0$ represents the evolution of x if the treatment continues exclusively using an arch wire and brackets orthodontic appliance. This evolution is typical of this type of orthodontic appliance, with an effectiveness progressively dropping off. The remaining treatment is the quickest, the target positioning being achieved at the moment $t_{S0}$. However, the duration for which an arch wire and brackets orthodontic appliance is worn ($t_{S0}-t_0$) is the longest.

Curve $S_1$ represents a first scenario for a hybrid treatment. According to this scenario, the arch wire and brackets orthodontic appliance hitherto worn is replaced, at the current moment, by an aligner. The switchover moment tai is therefore equal to $t_0$. The remaining treatment then continues exclusively using one or more aligners. The evolution of x is thenceforth substantially linear and illustrates the typical effectiveness of this type of orthodontic appliance.

The duration for which an arch wire and brackets orthodontic appliance is worn is advantageously zero. However, the remaining treatment is the slowest, the target positioning being achieved at the moment $t_{S1}$.

Curve $S_2$ represents a second scenario for a hybrid treatment. In this scenario, the arch wire and brackets orthodontic appliance is worn, during an arch-wire phase $P_{A2}$, until a switchover moment $t_{B2}$, and is then replaced with an aligner. The remaining treatment then continues exclusively using one or more aligners (aligner phase $P_{G2}$).

The duration for which an arch wire and brackets orthodontic appliance is worn ($t_{S2}-t_{B2}$) and the duration of the remaining treatment are somewhere between those of the previous two situations.

For preference, over 3, over 5, over 10, over 50 or over 100 hybrid remaining-treatment scenarios are determined.

The remaining-treatment scenarios may be determined by an orthodontist and/or by means of simulation software capable of simulating the effect of various orthodontic appliances according to the updated positioning of the teeth and the target positioning, for example using the Insignia™ software by the company Ormco™.

In step 6'), a profile is determined for each scenario determined in step 5'). A "profile" is made up of a set of values for evaluation parameters, namely ones which are relevant for evaluating a scenario according to an evaluation rule.

The evaluation parameters may relate to the duration, to the cost, to the pain and/or to the comfort and/or to the clinical severity associated with each scenario.

Pain may be measured by means of a pain factor associated with the treatment, for example evaluated from surveys taken from individuals who have been treated in a similar way.

Comfort in particular may make reference to the esthetic impact of the treatment. For example, the comfort factor may be the ratio between the total duration of the aligner phases and the total duration of the arch-wire phases for the remaining treatment.

The profile for scenario $S_1$ may for example be (duration of remaining treatment=3/10; comfort factor=9/10; pain factor=8/10; cost=7/10).

The profile for scenario $S_2$ may for example be (duration of remaining treatment=7/10; comfort factor=6/10; pain factor=5/10; cost=9/10).

In step 7'), the profiles are evaluated with reference to the evaluation rule. The evaluation rule is preferably established by the patient, according to the importance he attaches to the evaluation parameters. It may be established at any time before step 7').

For preference, the acquisition apparatus asks questions of the patient and the answers to these questions allow it to define the evaluation rule.

The preferred profile, with reference to the evaluation rule, is said to be "optimal".

An evaluation rule may establish a condition. For example, an evaluation rule may dictate that the duration of the remaining treatment be under 6 months or that the combined duration of the arch-wire phases of the full treatment must be under 2 months.

An evaluation rule may establish a conditional condition. For example, an evaluation rule may dictate that the duration of the remaining treatment be longer than 6 months or that the combined duration of the arch-wire phases of the residual treatment must not exceed 2 months.

An evaluation rule may establish an optimization rule. For example, an evaluation rule may dictate a search for the shortest remaining treatment, with the maximum duration of 1 month for treatment using an arch wire and brackets orthodontic appliance.

With this last example, scenario $S_2$ could prove optimal if the duration between $t_{B2}$ and $t_0$ is 1 month.

Of course, an evaluation rule may be complex and establish, for example, that the combined duration of the archwire phases in the remaining treatment be as short as possible, for a set total cost.

One evaluation rule could, in the example of FIG. 1, be to minimize the function $F=k_1*$Duration of remaining treatment$+k_2*$Comfort factor$+k_3*$Pain factor$+k_4*$Cost, the weightings $k_i$ preferably being determined by the patient or by an algorithm, according to the patients' responses to questions.

If $k_1=1$, $k_2=2$, $k_3=1$ and $k_4=3$, the function F for scenarios $S_1$ and $S_2$ is equal, respectively, to $F(S_1)=50$ and $F(S_2)=51$.

In step 8'), the evaluations of the profiles made in step 7') are compared so as to select a scenario considered to be optimal with reference to the evaluation rule. The switchover moment referred to as "optimal" $t_B*$ associated with this optimal scenario may then be proposed, for example displayed on a screen.

In the example of FIG. 1, $F(S_1)$ ($=50$) is less than $F(S_2)$ ($=51$). The profile of $S_2$ is therefore optimal, $S_2$ is the optimal scenario, and the switchover moment referred to as "optimal" $t_B*$ is therefore $t_{B2}$.

In a preferred embodiment, operations 5) to 7) are not performed successively. Operations 5) to 8) are preferably performed in the form of steps 5") to 8").

More specifically, a first scenario is determined and its profile evaluated before a second scenario is determined. The second scenario may thus advantageously be determined according to the evaluation of the first scenario.

For preference, the new remaining-treatment scenario is determined on the basis of scenarios the profiles of which have been evaluated beforehand. For example, if the two scenarios evaluated beforehand show that increasing the duration of the arch-wire phases impairs the score of the profiles with reference to the evaluation rule, for example because this rule is highly influenced by a comfort factor, the new scenario will be looked for among the scenarios that offer a low total duration for the arch-wire phases.

The search for an optimal scenario is thereby speeded up considerably. All known optimization methods can be used. The search for the optimal scenario preferably performed by means of a meta-heuristic, preferably evolutionary, method, preferably by simulated annealing, preferably by means of a method described in PCT/EP2015/074896.

Steps 5") to 8") are particularly suitable when the creation of scenarios and the evaluation of scenario profiles are automated in a simulator. For preference, such a simulator is programmed into a computation tool, for example a computer or an acquisition apparatus, into which the evaluation rule has been programmed.

A scenario simulator may be created from statistical analyses of historical data. In particular, a statistical analysis of historical data may be used to simulate the effect of a given orthodontic appliance on the positioning of the teeth, but also to define a profile, for example a pain factor or comfort factor for the remaining treatment according to the duration of the arch-wire phases or an overall-treatment cost according to the durations of the arch-wire and aligner phases.

In one preferred embodiment, the method comprises a step 9) in which the optimal scenario and/or the optimal profile, are presented to the patient, preferably on a screen, preferably on the screen of his mobile telephone. Of course, the method may lead to several optimal scenarios being determined. For preference, all the optimal scenarios and/or optimal profiles are presented to the patient, preferably on the acquisition apparatus used in step 3).

If the patient is not satisfied, he may establish a new evaluation rule, for example by modifying the weightings $k_i$, and resume the method at step 5') or 5").

The optimal switchover moment for the optimal scenario adopted allows the remaining treatment to be adapted precisely to the needs of the patient. In particular, it is possible to manufacture one or more aligners which could be used from this moment on.

As is now clearly apparent, the invention provides an effective way for optimizing a hybrid orthodontic treatment according to an evaluation rule. Advantageously, this evaluation rule may take into consideration numerous evaluation parameters, making it possible precisely to respond to the specific expectations of the patient. Finally, a method according to the invention may be programmed, particularly onto a mobile telephone. At any moment, the patient may, remotely, perform evaluations of various scenarios and decide accordingly when to switch over. The method may be implemented as many times as desired, for example more than once, more than twice or more than five times per month.

The number of orthodontist appointments is also advantageously limited.

The invention claimed is:

1. A method of determining an optimal switchover moment for a hybrid orthodontic treatment of teeth of a patient, said method comprising the following operations:
    1) at the start of the treatment or before the start of the treatment, creating a digital three-dimensional model of at least part of a dental arch bearing said teeth, "initial reference model" and, for each of said teeth, defining a digital three-dimensional reference model of said tooth in the initial reference model, called "tooth model";
    2) after operation 1), deforming the initial reference model, by moving the tooth models, until said tooth models are in a target position, so as to obtain a "target reference model",
    3) after operation 2), at some moment in a phase of the treatment during which the patient wears an arch wire and brackets orthodontic appliance, referred to as "current moment", acquiring, by means of an image acquisition apparatus, at least one two-dimensional image of said teeth, referred to as "updated image", under the actual acquisition conditions;
    4) deforming the initial reference model, by moving the tooth models, until said at least one updated image corresponds to a view of the initial reference model thus deformed, referred to as "updated reference model";
    5) determining, from said updated reference model and from said target reference model, a plurality of remaining-treatment scenarios for moving said teeth from their position represented in the updated reference model into their position represented in the target reference model, each scenario comprising, from a switchover moment onwards, at least one phase of treatment using an orthodontic aligner;
    6) determining, for each scenario, a profile comprising at least one value for an evaluation parameter selected from the group formed of:
        the duration of the remaining treatment of said scenario;

the duration of the entire treatment;
a clinical-complexity factor, or "severity score";
a pain factor for the remaining treatment of said scenario,
a pain factor for the entire treatment;
the duration of the phase or phases of treatment using an arch wire and brackets orthodontic arch wire during the remaining treatment;
a comfort factor for the remaining treatment of said scenario,
a comfort factor for the entire treatment;
a cost of the remaining treatment of said scenario,
a cost of the entire treatment,
a function of the preceding evaluation parameters;
7) evaluating each profile by means of an evaluation rule; and
8) determining, from the scenario the profile of which is optimal, or "optimal scenario", an optimal switchover moment for replacing the arch wire and brackets orthodontic appliance with an aligner.

2. The method as claimed in claim 1, in which over 50 scenarios are determined in operation 5).

3. The method as claimed in claim 1, in which operations 5) to 8) are imbricated, the operations 5) to 8) being performed by executing the following steps 5") to 8"):
5") determination, from said updated reference model and from said target reference model, of a remaining-treatment scenario for moving said teeth from their position represented in the updated reference model into their position in the target reference model, a remaining-treatment scenario comprising, from a switchover moment onwards, at least one phase of treatment using an orthodontic aligner;
6") determination, for said scenario, of a profile comprising at least one value for an evaluation parameter selected from the group formed of:
the duration of the remaining treatment of said scenario;
the duration of the entire treatment;
a clinical-complexity factor, or "severity score";
a pain factor for the remaining treatment of said scenario,
a pain factor for the entire treatment;
the duration of the phase or phases of treatment using an arch wire and brackets orthodontic arch wire during the remaining treatment;
a comfort factor for the remaining treatment of said scenario,
a comfort factor for the entire treatment;
a cost of the remaining treatment of said scenario,
a cost of the entire treatment,
a function of the preceding evaluation parameters;
7") evaluation of the profile by means of at least one evaluation rule and, if the profile is not optimal with reference to the evaluation rule, determination of a new remaining-treatment scenario and resumption from step 6");
8") determination, from the scenario the profile of which is optimal, or "optimal scenario" of an optimal switchover moment for replacing the arch wire and brackets orthodontic appliance with an aligner.

4. The method as claimed in claim 1, in which, in operation 3), the image acquisition apparatus is selected from the group consisting of a mobile telephone, a connected camera, a smartwatch, a tablet and/or a desktop or laptop personal computer.

5. The method as claimed in claim in which operation 4) comprises the following steps:
c) analysis of the updated image and creation of an updated map relating to discriminating information;
e) search, in the case of the updated image, for an updated reference model corresponding to the positioning of the teeth at the time of the acquisition of the updated image.

6. The method as claimed in claim 5, in which step e) comprises the following steps:
e1) definition of a reference model o be tested as being the initial reference model, then
e2) following the subsequent steps, testing virtual acquisition conditions with the reference model to be tested in order to achieve a fine approximation of said actual acquisition conditions;
e21) determining virtual acquisition conditions to be tested;
e22) creation of a two-dimensional reference image of the reference model to be tested under said virtual acquisition conditions to be tested;
e23) processing of the reference image to create at least a reference map at least partially representing said discriminating information;
e24) comparison of the updated and reference maps so as to determine a value for a first evaluation function, said value for the first evaluation function being dependent on the differences between said updated and reference maps and corresponding to a decision as to whether to continue or stop the search for virtual acquisition conditions approximating said actual acquisition conditions with greater precision than said virtual acquisition conditions to be tested as determined the last time step e21) was run;
e25) if said value for the first evaluation function corresponds to a decision to continue said search, modification of the virtual acquisition conditions to be tested, then resumption from step e22);
e3) determination of a value for a second evaluation function, said value for the second evaluation function being dependent on the differences between the updated and reference maps under the virtual acquisition conditions best approximating said actual acquisition conditions and resulting from the last running of step e2), said value for the second evaluation function corresponding to a decision to continue or stop the search for a reference model approximating the positioning of the teeth at the time of the acquisition of the updated image with greater precision than said reference model to be tested that was used the last time step e2) was run, and if said value for the second evaluation function corresponds to a decision to continue said search, modification of the reference model to be tested by moving one or more tooth models, followed by resumption from step e2).

7. The method as claimed in claim 6, comprising a step 9) in which the optimal switchover moment are presented to the patient.

8. The method as claimed in claim 6, in which, in step 1), a digital three-dimensional reference model is defined for a gum from which said tooth models emerge, or "gum model", and, in step 4), said tooth models are moved and said gum model is modified to deform the initial reference model.

9. The method as claimed in claim 8, in which, in order to deform the initial reference model a deformation of the gum model is calculated from said movements of said tooth models.

10. The method as claimed in claim 1, in which, the scenarios comprise different switchover moments.

11. A system comprising an image acquisition apparatus and a computation tool comprising a computer program comprising program code instructions for executing operations 4) to 8), when said program is run after the acquisition by means of the image acquisition apparatus, at some moment in a phase of a treatment during which a patient wears an arch wire and brackets orthodontic appliance, referred to as "current moment", of at least one two-dimensional image of said teeth, referred to as "updated image", under actual acquisition conditions:
   4) deforming an initial reference model, creating at the start of the treatment or before the start of the treatment, for each of said teeth of the initial reference model, digital three-dimensional reference model of said tooth in the initial reference model being defined, called "tooth model";
   the deformation of the initial reference model being carried out by moving the tooth models, until said at least one updated image corresponds to a view of the initial reference model thus deformed, referred to as "updated reference model";
   5) determining, from said updated reference model and from a target reference model, a plurality of remaining-treatment scenarios for moving said teeth from their position represented in the updated reference model into their position represented in the target reference model, each scenario comprising, from a switchover moment onwards, at least one phase of treatment using an orthodontic aligner;
   6) determining, for each scenario, a profile comprising at least one value for an evaluation parameter selected from the group formed of:
      a duration of the remaining treatment of said scenario;
      a duration of the entire treatment;
      a clinical-complexity factor, or "severity score";
      a pain factor for the remaining treatment of said scenario,
      a pain factor for the entire treatment;
      a duration of the phase or phases of treatment using an arch wire and brackets orthodontic arch wire during the remaining treatment;
      a comfort factor for the remaining treatment of said scenario,
      a comfort factor for the entire treatment;
      a cost of the remaining treatment of said scenario,
      a cost of the entire treatment,
      a function of the preceding evaluation parameters;
   7) evaluating each profile by means of an evaluation rule; and
   8) determining, from the scenario the profile of which is optimal, or "optimal scenario", an optimal switchover moment for replacing the arch wire and brackets orthodontic appliance with an aligner.

12. The system as claimed in claim 11, wherein said computational tool further comprises a scenario simulator able to create scenarios, to determine profiles of said scenarios, and to evaluate said scenarios with reference to an evaluation rule.

13. The system as claimed in claim 12, wherein said computational tool further comprises an interface and means for determining the evaluation rule from data input using said interface.

14. A method of determining an optimal switchover moment for a hybrid orthodontic treatment of teeth of a patient, said method comprising the following operations:
   1) at the start of the treatment or before the start of the treatment, creating a digital three-dimensional model of at least part of a dental arch bearing said teeth, called "initial reference model" and, for each of said teeth, defining a digital three-dimensional reference model of said tooth in the initial reference model, called "tooth model";
   2) after operation 1), deforming the initial reference model, by moving the tooth models, until said tooth models are in a target position, so as to obtain a "target reference model";
   3) after operation 2), at some moment in a phase of the treatment during which the patient wears an arch wire and brackets orthodontic appliance, referred to as "current moment", acquiring, by means of an image acquisition apparatus, at least one two-dimensional image of said teeth, referred to as "updated image", under the actual acquisition conditions, the acquisition is performed by the patient or someone close to the patient;
   4) deforming the initial reference model, by moving the tooth models, until said at least one updated image corresponds to a view of the initial reference model thus deformed, referred to as "updated reference model";
   5) determining, from said updated reference model and from said target reference model, a plurality of remaining-treatment scenarios for moving said teeth from their position represented in the updated reference model into their position represented in the target reference model, each scenario comprising, from a switchover moment onwards, at least one phase of treatment using an orthodontic aligner, the scenarios being determined automatically by a scenario simulator;
   6) determining, for each scenario, a profile comprising at least one value for an evaluation parameter selected from the group formed of:
      the duration of the remaining treatment of said scenario;
      the duration of the entire treatment;
      a clinical-complexity factor, or "severity score";
      a pain factor for the remaining treatment of said scenario;
      a pain factor for the entire treatment;
      the duration of the phase or phases of treatment using an arch wire and brackets orthodontic arch wire during the remaining treatment;
      a comfort factor for the remaining treatment of said scenario;
      a comfort factor for the entire treatment;
      a cost of the remaining treatment of said scenario;
      a cost of the entire treatment;
      a function of the preceding evaluation parameters;
   7) evaluating each profile by means of an evaluation rule; and
   8) determining, from the scenario the profile of which is optimal, or "optimal scenario", an optimal switchover moment for replacing the arch wire and brackets orthodontic appliance with an aligner.

15. The method as claimed in claim 14, in which, the evaluation rule being established by the patient.

* * * * *